United States Patent [19]

Symes et al.

[11] Patent Number: 4,778,880

[45] Date of Patent: Oct. 18, 1988

[54] PROCESS FOR PRODUCING DERIVATIVES OF HYDROXY COMPOUNDS, THE PRODUCTS AND THEIR USES

[76] Inventors: Kenneth C. Symes, 4 Silk Mill Drive, East Mortin, Keighley, West Yorkshire; Kishor K. Mistry, 69 Beckside Road, Lidget Green, Bradford, West Yorkshire, both of England

[21] Appl. No.: 780,566

[22] Filed: Sep. 26, 1985

[30] Foreign Application Priority Data

Sep. 28, 1984 [GB] United Kingdom ............... 8424500
Jan. 29, 1985 [GB] United Kingdom ............... 8502145

[51] Int. Cl.$^4$ ..................... C08B 11/14; C08B 31/12
[52] U.S. Cl. ............................. 536/43; 536/50; 522/31; 522/42; 522/88; 525/58; 526/238.2; 526/238.21; 526/238.22; 526/238.23; 528/246
[58] Field of Search ............ 526/238.2, 238.21, 238.22, 526/238.23; 536/43, 50; 525/58; 528/246

[56] References Cited

U.S. PATENT DOCUMENTS

| | | | |
|---|---|---|---|
| 2,837,511 | 6/1958 | Mantell | 536/43 |
| 3,135,738 | 6/1964 | Cushing | 536/50 |
| 4,079,025 | 3/1978 | Young | 526/238.22 |
| 4,115,332 | 9/1978 | Young | 526/238.22 |
| 4,129,722 | 12/1978 | Iovine | 536/43 |
| 4,451,613 | 5/1984 | Rousseau | 526/238.22 |
| 4,511,646 | 4/1985 | Fohrenkamm | 526/238.2 |
| 4,557,951 | 12/1985 | Verbanac | 536/43 |

FOREIGN PATENT DOCUMENTS

42-11918 7/1967 Japan .
1056079 1/1967 United Kingdom .

*Primary Examiner*—C. Warren Ivy

[57] ABSTRACT

A process for producing novel water-soluble compounds of the formula $(HO)_m$—A—$(OCH_2NR^1COR)_p$ comprises forming a dispersion of an aqueous solution of a substrate $A(OH)_n$ which is an alcohol or, preferably, a carbohydrate and a derivatising reagent $HOCH_2NR^1COR^2$ in a water immiscible liquid and azeotroping the dispersion to remove water and thereby to drive the condensation reaction. The process can achieve high degrees of substitution and is of particular use in the production of water-soluble unsaturated polymersable products, preferably methylol acrylamide derivatives, in a process in which the aqueous dispersed phase contains a water-soluble polymerisation inhibitor. The unsaturated products may be used as cross-linking monomers in many aqueous polymerisation reactions, for instance an aqueous composition containing them with a water-soluble photo-initiator system including a dye are used as curing inks.

12 Claims, No Drawings

PROCESS FOR PRODUCING DERIVATIVES OF HYDROXY COMPOUNDS, THE PRODUCTS AND THEIR USES

This invention relates to processes for producing derivatives of a hydroxy compound and the products of such a process.

There are many processes and techniques known for producing derivatives of polysaccharides such as starches, cellulose and guar gum to modify their properties. For example, such compounds may be made ionic or provided with different solubility characteristics, film forming, dispersant, coagulant, or other properties.

In conventional derivatisation reactions of polysaccharides, the processes are conducted in homogeneous or heterogeneous systems. In homogeneous systems, the reaction is conducted in very dilute solutions of the polysaccharide. The concentration cannot be increased because of the viscosity. Yields, per unit volume, are therefore very low and the degree of substitution is generally low.

In heterogeneous systems, the starch or other polysaccharide may be reacted with the derivatising reagent in a dry, semi-dry or slurry process. The starch or other granules may be swollen but in many processes swelling is deliberately restrained, for instance by adding salt. These processes can all be difficult to operate and generally lead to low degrees of substitution.

U.S. Pat. No. 4,079,125 describes a process, for adding ethylenically unsaturated groups to starch molecules. For an efficient process it is necessary for the process to be conducted at a high solids content in the reaction mixture. The process exemplified in the specification is a semi-dry process in which water-insoluble starch is formed into a dough with water containing the derivatising reagent and a polmerisation inhibitor. Since the reaction mixture is heterogeneous, efficient dispersion of the polymerisation inhibitor is difficult so that homopolymerisation, graft copolymerisation and cross linking of the starch molecules take place, reducing the efficiency of the derivatisation and rendering the product insoluble.

It is suggested in the specification that a similar process could be carried out in solution. However the solvent is not specified and since the reaction is a condensation involving elimination of water, it would be necessary to use non-aqueous solvents such as N,N-dimethylformamide or dimethyl sulphoxide. These high boiling aprotic solvents are expensive and considerably add to the difficulty of product recovery.

Although it is also suggested that the method is suitable for use with low molecular weight substrates, in practice mixtures of reagents containing dissolved or partially dissolved substrates like hydrolysed starch are extremely difficult to process and to fully and evenly dehydrate.

The alternative route to lower molecular weight acrylamidomethyl starch derivatives described in U.S. Pat. No. 4,079,025 is to prepare the high molecular weight derivative first and then to de-polymerise. This is complicated by the fact that the pendant groups can also be removed under the conditions of hydrolysis leading to lower DS or even total loss of polymerisable side-chains. Mild enzymic hydrolysis is therefore preferred but this particular method of hydrolysis is not applicable to highly substituted starch molecules since the starch chains are no longer susceptible to enzymic attack.

In short, the method taught in U.S. Pat. No. 4,079,025 is inappropriate for the manufacture of low molecular weight derivatives especially when products of high levels of substitution are needed.

It is also known to react ionic methylol amides on-to insoluble cellulose in an aqueous slurry process similar to that described in U.S. Pat. No. 4,075,025.

In UK Specification No. 1,413,301, there is disclosed a method of adding acrylamide to a starch in an aqueous solution reaction in which the starch concentration in the reaction mixture is always less than 20%. The amide groups of the starch derivative are further reacted with formaldehyde and an amine by a Mannich reaction to produce a cationic product. The concentration and yield of the desired product is low and the product itself is unstable since the reaction is reversible. In addition, the reaction mixture often gels because of cross-linking and other side reactions between the formaldehyde and amide groups.

The present invention is concerned with condensation reactions. It is of course well known that various condensation reactions, such as esterification of an alcohol with an acid, can be promoted by removing water of condensation during the reaction. For instance in the field of ultraviolet-curable inks it is known (European Patent Specification No. 0103684A) to esterify an acetal glycol with acrylic acid in an inert solvent in which all the reactants and end products dissolve (the reaction mixture thus being homogeneous) and to remove the water of condensation by azeotroping during the process.

Another process for forming substituted polysaccharide is described in U.S. Pat. No. 4,129,722. The process is carried out in a continuous medium of water-immiscible oil in which the polysaccharide is dispersed and in which are suspended droplets of aqueous reagent solution. Surfactant is added to reduce the water dispersibility of the polysaccharide and prevent it from partitioning into the aqueous phase. The reactions described are all substitution reactions, in which an ionic compound such as hydrogen chloride is released, or addition reactions in which the polysaccharide is added across a carbon-carbon double bond, for example across the ethylenically unsaturated bond of acrylic acid. Apparently the described process does not lead to the formation of an ester between the polysaccharide and acrylic acid. Various other addition reactions are described. After completion of the reaction, the mixture may be dehydrated by a conventional azeotropic distillation.

We have now found that a particular derivatising reaction for producing derivatives of substrates containing hydroxyl groups can be conducted in an effective and simple manner to produce a wide range of products useful in a variety of applications. In particular the new process is capable of providing novel soluble product of for instance carbohydrates, such as starch derivatives, having degrees of substitution higher than has been possible using the conventional processes.

In the invention, we provide a process for producing a compound of the formula $(HO)_m$—A—$(OCH_2NR^1COR)_p$ from a substrate $A(OH)_n$ and a derivatising reagent $HOCH_2NR^1COR^2$ in which $A(OH)_n$ is an alcohol ($n=1$), a glycol ($n=2$), a polyol ($n=3$ or more) or a carbohydrate and either is a polar liquid that is miscible with water at a temperature below the boiling point of water and has a higher boiling point than water, or is a solid in which water is wholly miscible or is water soluble at a temperature below the boiling point of water, and in which the derivatising reagent is soluble in an aqueous mixture of $A(OH)_n$, R is an alkyl or an alkenyl group, which is unsubstituted or substituted by one or more non-ionic, anionic or cationic groups, $R^1$ is a hydrogen atom or a $C_{1-4}$ alkyl group, $R^2$ is selected from the groups represented by R, n is 1 or higher, m is zero or higher, p is 1 or higher and $m+p=n$, and the process is characterised in that the process is a condensation reaction and is effected by forming a dispersion in a water-immiscible solvent of an aqueous solution of the compound $A(OH)_n$ containing the derivatising reagent and azeotroping the reaction mixture to remove water and thereby drive the condensation reaction.

The use of the specified reagent appears critical for a condensation reaction to occur since other reagents seem to be incapable of reacting. The final product may be the product of the single stage reaction of the derivatising reagent with the substrate $A(OH)_n$, and in this case the group R of the final product is the same as the group $R^2$ of the derivatising reagent it may be a saturated ionic group. Alternatively, the process may initially produce a product which is a compound of the formula $(HO)_m$—A—$(OCH_2NR^1COR^2)$ and this is further reacted to the final product by conversion of the group $R^2$ to the group R.

The derivatising reagent may be formed in situ by the reaction of an amide $R_2CONR^1H$ with formaldehyde. In this case, of course, if the amide and formaldehyde are reacted together in the presence of the substrate $A(OH)_n$ then the intermediate methylolamide derivatising reagent may not be able to be isolated from the reaction mixture but may react instantaneously with the hydroxy compound and possibly the formaldehyde will react with the substrate before the amide reacts or vice versa.

It is preferable to form the derivatising reagent in an earlier reaction step, from which the methylolamide compound is isolated. This multistage process is preferred since optimum conditions for the reaction of the amide and formaldehyde are different from those required for the condensation reaction. The reaction of the amide and formaldehyde is preferably carried out in basic conditions, whereas the derivatising reaction is carried out under acidic conditions.

The derivatising reagent (or the amide if the reagent is made in situ) must be soluble in the aqueous phase of the reaction mixture, which comprises the substrate and water. Thus the reagent must not partition into the non-aqueous continuous phase to an extent that a substantial portion becomes inaccessible to the aqueous phase. Preferably the reagent is less volatile then water and the non-aqueous liquid of the continuous phase so that it does not easily codistil with the azeotrope.

$R^1$ is generally alkyl, preferably methyl or, preferably hydrogen.

The group $R^2$ may represent an alkenyl group, usually $C_{2-8}$, preferably $C_{2-4}$ and it is preferably unsubstituted. The alkenyl group may be isopropenyl and is preferably vinyl group. Preferred derivatising reagents are methylol acrylamide and methylol methacrylamide.

Products formed from a derivatising reagent having an unsaturated group $R^2$ may be reacted in a further stage to convert some or all of the groups $R^2$ to a saturated group R, generally by adding a group across the double bond of the group $R^2$. The resultant group R may contain a non-ionic, anionic or cationic group, for instance any of those described below for the group $R^2$. A product in which a group R contains a non-ionic hydrophobic group is suitably formed by a 2 stage reaction, such as reacting an unsaturated derivative of the substrate with a higher, e.g., a $C_{4-30}$ alkyl, aryl, alkaryl or aralkyl thiol. The two stage reaction is preferred in this case since a derivatising reagent comprising a lipophilic group would tend to partition into the continuous non-aqueous phase of the reaction mixture and would not react with the substrate.

The group $R^2$ may be a lower alkyl group preferably containing 1 to 4 carbon atoms. The group may be substituted by an anionic group, for example a carboxylic acid, a sulphonic acid, a sulphuric acid or a phosphorus-containing acid group or any of their water soluble salts. For example, the reagent may be $NaO_3SCH_2CH_2CONHCH_2OH$.

The alkyl group $R^2$ may be substituted by a cationic group, for example a primary, secondary or tertiary amine group or an acid addition salt or quaternary derivative thereof. For example, the reagent may be $Cl^-(H_3C)_3N^+CH_2CH_2$—$CONHCH_2OH$.

Group $R^2$ may be substituted by groups containing heteroatoms, such as halogen, oxygen, sulphur or nitrogen atoms. $R^2$ may comprise hydroxy groups or hetero cyclic groups, such as a morpholine group. The group $R^2$ must be such that the reagent is water-soluble as discussed above.

It is particularly preferred to conduct the process in the presence of two or more different derivatising reagents to produce a product having two or more different groups R. For instance, the compound $A(OH)_n$ may be reacted with an ionic saturated derivatising reagent and an unsaturated derivatising reagent, thereby producing a compound that is both ionic and polymerisable. Alternatively, the substrate may be reacted with two different ionic derivatising reagents, e.g., comprising an amine group in its free base form and a quaternary derivative of the same compound.

The substrate $A(OH)_n$ may be a carbohydrate of high molecular weight, e.g. $10^4$ to $10^6$, that is water soluble. Dextrins are preferred, especially yellow dextrins. Broadly it may be selected from water soluble monosaccharides, sugar alcohols and di- or other poly-saccharides. It may be a lower molecular weight saccharide or other carbohydrate e.g. $10^3$ to $10^4$ molecular weight. It may be cellulosic, e.g. hydroxyethyl cellulose or a gum, e.g. guar gum. It may be a synthetic hydroxyl substituted polymer, e.g. polyvinyl alcohol. It may be lower molecular weight compound, e.g. below $10^3$, provided that it has (if liquid) a boiling point above the boiling point of water. For instance, it may be a monohydric alcohol (e.g. neopentyl alcohol or ethylene glycol monobutyl ether) or a dihydric or trihydric alcohol (e.g. glycerol or polyethylene glycol) or a polyhydric alcohol (e.g. sucrose, sorbitol, hexitol or pentaerythritol).

Preferably the substrate $A(OH)_n$ is a polysaccharide or other carbohydrate of molecular weight above 1,000 and preferably above 10,000 and particular benefit is attained when $A(OH)_n$ is a carbohydrate that will form a viscous aqueous solution. Preferably it is a dextrin.

The concentration of the compound $A(OH)_n$ in the aqueous phase is generally as high as possible to maximize productivity. It is usually above 20% and preferably above 40%. For example, for starches the concentration is at least 10% by weight and usually at least 20% by weight. For dextrins the concentration is generally at least 20% by weight and preferably between 40 and 60% by weight. The maximum concentration is generally below 80%, usually below 60%, and is dependent upon the viscosity of the resultant dispersion or solution which must be mobile enough for a suspension of small beads to be created in the continuous oil phase.

An important advantage of the reaction being homogeneous in the aqueous phase is that when the derivatising reagent comprises an unsaturated compound, a water-soluble polymerisation inhibitor can be dissolved or dispersed throughout the reaction phase to prevent polymerisation and cross-linking reactions during the condensation reaction. These reactions are undesirable since the product is heterogeneous, difficult to isolate, insoluble and be commercially unsatisfactory.

The polymerisation inhibitor preferably comprises copper (II) in an amount of at least 1 ppm, preferably 5 or 10 ppm, often at least 100 ppm, and sometimes 2,000 ppm or more. Other conventional inhibitors which do not migrate entirely to the continuous phase may be used in effective amounts, for example hydroquinone may be used at concentrations of at least 500 ppm. Other suitable inhibitors are paramethoxyphenol, methyleneblue and phenylthiazine. The inhibitor may be removed, if necessary, in a subsequent step but may often be left in the product. Copper (II) ions or other metal ions may be removed by contacting an aqueous solution of the product with an ion exchange resin.

The aqueous dispersed phase generally comprises a condensation catalyst. For the reaction of a compound $A(OH)_n$ with a methylol amide, the catalyst is preferably an acid (often an acid generating) catalyst. This may be, for instance, ammonium dihydrogen phosphate, ammonium chloride or paratoluene sulphonic acid. The concentration of an acid catalyst in the aqueous phase is generally sufficient to generate a pH of less than 6 and preferably less than 5. For example, the concentration of ammonium compounds is generally at least 0.1% by weight based on the total aqueous phase, generally at least 0.5% by weight and preferably at least 2% by weight. Paratoluene sulphonic acid is generally used at lower concentrations, for example less than 1%, or even less than 0.1% by weight.

Water-immiscible liquids used in the process of the invention are inert and generally non-solvents for the starting materials and for the products. Preferably the liquids are non-toxic. The liquid should be suitable for azeotroping off with water. Suitable examples are aliphatic, aromatic or naphthenic hydrocarbon liquids or oils, chlorinated hydrocarbons and aromatic or higher aliphatic esters such as fatty glycerides, dibutyl phthalate and dioctyl phthalate or mixtures of any of these. The liquid should include a volatile component capable of forming an azeotrope.

The reaction mixture may be a water-in-oil emulsion, but is preferably a dispersion of aqueous beads in oil. The particle size at the beginning of the reaction is selected within the range of 0.2 to 2000, preferably 20 to 500, microns by appropriate choice of the degree of agitation, and the amount and type of emulsifier if present. For particles sizes above 50 microns, stabiliser is used generally in an amount of 0.01 to 0.5% by weight, preferably 0.03 to 0.2% by weight, based on the weight of solids in the aqueous phase and emulsifier may be absent.

For smaller particles, e.g., in the size range 0.5 to 5 microns in diameter, water-in-oil emulsifier is generally used in an amount in the range 0.1 to 10%, preferably 0.5 to 5%, by weight of the total weight of the aqueous phase with a stabiliser. A stabiliser is used in an amount of from 0.05 to 10, preferably 0.5 to 5% by weight based on the total weight of the aqueous phase.

The dispersed phase generally comprises between 25 and 75% of the total volume of the reaction mixture.

The stabilizer may be an oligomeric or polymeric material and can generally be defined as amphipathic. Normally the stabiliser is a copolymer of one or more hydrophobic monomers and one or more hydrophilic monomers, for example it may be a polyhydroxy stearic acid-polyethylene glycol condensate, maleic polymer or a copolymer of hydrophilic and hydrophobic acrylic monomers, for example a copolymer of stearyl methacrylate and methacrylic acid or other stabilisers described in GB No. 1482515, U.S. Pat. No. 4,339,371, EP No. 0126528 and EP No. 0102760. Water-in-oil emulsifiers may be for instance sorbitan monostearate, sorbitan monooleate, glyceryl monooleate or ethoxylated fatty alcohols.

Generally under the conditions of the reaction, the $A(OH)_n$ substrate is not substantially depolymerised, for instance a dextrin or other carbohydrate backbone will remain polymeric although some reduction of viscosity compared to the starting polysaccharide may be observed.

The process may be performed by forming a dispersion or solution of the substrate in water and adding to the resultant mixture any catalyst, polymerisation inhibitor and then the derivatising reagent. The aqueous mixture is dispersed into the water-immiscible liquid containing stabiliser and/or emulsifier with agitation at a suitable temperature. This may be room temperature but in some instances, for instance if the solution is very viscous at room temperature, it may be advantageous to use higher temperatures, for example up to about 90° C., generally about 80° C. For most substrates it is preferable to dissolve the substrate in the aqueous reaction mixture before it is dispersed into the water immiscible liquid. However, for high molecular weight substrates which form highly viscous aqueous solutions, it is convenient for the substrate to be in dispersed form when the aqueous phase is dispersed into the water immiscible liquid. Thus the substrate may not be completely dissolved until the temperature is raised to the reaction temperature.

The mixture is agitated to create a suspension of aqueous droplets and is generally heated to the required temperature at which azeotroping occurs and at which the substrate is substantially completely dissolved or mixed in the aqueous reaction phase. The temperature of the reaction may for instance be at least 60° C., generally at least 70° C. and often at least 80° C. The distillation is generally carried out under reduced pressure and is usually continued until no further water is collected. The total reaction time is normally about half to 5 hours, often about 2 hours.

Azeotroping the reaction mixture removes a mixture of water from the aqueous phase and volatile oil from the continuous phase. Azeotroping therefore drives the equilibrium towards the product side by removing one of the products (water) from the mixture. Where the reaction mixture comprises an aqueous phase which is fairly dilute, there is usually little or no reaction before the azeotroping has removed at least some of the water. Azeotroping is generally carried out until substantially all the water has been removed from the reaction mixture, to leave the product as solid particles dispersed in oil. The product may be used as it is, or the dry particles may be separated from the oil by conventional processes especially when the particles are beads having a size above 50 microns.

Although the process of the invention can be conducted to give low substitution, it is of particular value in the production of products with high substitution levels since such levels have not previously been possible. For instance at least 10%, and often at least 20% or 30%, and even up to 100%, of the hydroxyl groups may be substituted. For polysaccharides, the degree of substitution is preferably at least 0.1 and is often at least 0.3 and sometimes as high as 0.5 or even up to 1.

The process of the invention can be used to make a wide variety of products, but is of particular value for making cold-water soluble products. For these, cross-linking must not occur and either the substrate must be cold water soluble or must become cold water-soluble during the reaction.

In the context of this specification, cold water soluble means that the material can be completely dissolved in water at 20° C. to form a true solution or stable colloidal solution with no solid residue. If, in any particular test, the amount of water is too low to dissolve all the residue (because of the high viscosity of the resultant solution) more water should be added to check that the residue is truly insoluble, i.e. even at infinite dilution. Preferably the polymerisable material of the invention will form a true solution in cold water at 20%, preferably at 30% and most preferably at 40% by weight concentration or more.

A cold water-soluble compound of the invention has the formula $(HO)_m A(OCH_2NR^1COR)_p$ in which A is derived from a substrate $A(OH)_n$ in which n is 1 or more which is an alcohol (n=1), glycol (n=2), polyol (n=3 or more) or a carbohydrate and either is a polar liquid that is miscible with water below the boiling point of water and has a boiling point higher than the boiling point of water or is a solid that is water soluble at a temperature below the boiling point of water, R is an alkyl or an alkenyl group which is unsubstituted or substituted by one or more non-ionic, anionic or cationic groups and $R^1$ is a hydrogen atom or a $C_{1-4}$ alkyl group, m is zero or higher, p is 1 or higher and $n=m+p$.

In one preferred group of novel products, R represents an alkenyl group having from 2 to 4 carbon atoms and is preferably vinyl or isopropenyl. These latter preferred compounds are derivatives of methylol acrylamide and methylol methacrylamide.

The products of the invention differ from the products of U.S. Pat. No. 4,079,025 in that, inter alia, they are cold water soluble, they are made from a compound $A(OH)_n$ that is water soluble, and they can have wide ranges of functionality with from 0.001 to 100% of the hydroxy groups substituted by the unsaturated groups. Where $A(OH)_n$ is a polysaccharide, the degree of substitution (DS) may be up to 3.

The extent of substitution depends primarily on the relative proportions of the reagents in the reaction mixture and also on the reaction conditions, for example the degree of acidity of the reaction mixture, the acid generating catalyst used, the temperature and the reagents. The new unsaturated products are preferably substantially free of cross-linking between pendant unsaturated groups on different substrate molecules or between an unsaturated pendant group and another group on a different substrate molecule. The products are also preferably free from graft chains of the methylolacrylamide. Such reactions of the ethylenically unsaturated bonds are wasteful since the products of such reactions either do not contribute in a beneficial manner to the properties of the product or adversely affect the properties. Cross-linking will decrease the water solubility of the products and this is undesirable.

The substrate may be any of those mentioned above as preferred substrates for carrying out the novel process.

One range of preferred products are those in which $A(OH)_n$ is a carbohydrate having a molecular weight of more than $10^4$. These may have a degree of substitution (DS) of at least 0.01, but generally less than 0.1 We describe these as high mw low DS products.

Another preferred range of products are derived from carbohydrates having a molecular weight of at least $10^4$ and have a DS of at least 0.1 and usually at least 0.2, sometimes more than 0.5 up to the maximum DS. These products are described as high mw high DS.

A third preferred range of products have a molecular weight less than $10^4$, preferably less than 1000. The substrates are preferably carbohydrates, for example consisting of one or more carbohydrate residues, but may also be other polyols, glycols or alcohols. The degree of substitution of a carbohydrate substrate, for instance, may be from 0.005 up to the maximum degree of substitution, but generally the DS is less than 2.

Generally products prepared from polyhydric alcohols, carbohydrates etc. will contain at least a small proportion composed of molecules bearing at least two pendant groups but monofunctional products, containing a single pendant group, can be made from a monohydric alcohol.

The novel products of the invention can have a wide range of physical and chemical properties and for optimum results, the preparation and storage procedures will have to be selected having regard to the physical and chemical properties of the products. For instance when preparing highly substituted unsaturated products, especially those from very low molecular weight carbohydrate, higher levels of inhibitor (up to 200–2000 ppm on aqueous phase) may be necessary than for lower degrees of substitution. Without this inhibition, polymerisation may occur during azeotroping, e.g., at about 80% dehydration, and this will lead to coagulation and/or to isolation of insoluble particles. Although many products can be stored as dry particles, the low molecular weight high DS particles tend to absorb moisture and become sticky, and so these products are best stored as aqueous concentrates. Also, dry particles of such compounds where R is unsaturated may tend to partially polymerise to give a fused hard mass but there is less risk of homopolymerisation occurring in solution.

The invention also includes polymer made from the polymerisable products. The polymer may be homopolymer or copolymers with other monomers, for instance with acrylamide, acrylic acid, or dialkylaminoalkyl acrylates. The molecular weight and the degree of substitution, together with the comonomers, determines the properties of the resultant polymer. Lower DS products will polymerise to give highly water swellable products which may be useful in, for instance, the immobilisation of enzymes.

High DS products give highly cross-linked gels useful for chemical grouting, for instance for controlling water permeation in subterranean strata by in situ polymerisation. One application is the injection into porous substrates, for instance in the region of sewers, to decrease the water permeability of the substrates and to increase their structural strength. In situ polymerisation of the products may be used to reduce dust from spoil heaps by capping the heaps, that is by applying a polymerisable composition to the top layer of a spoil heap and allowing it to polymerise, the reaction suitably being initiated by light.

The polymerisable products are also of use in the gelling of aqueous suspensions or dispersions. For example, emulsions of hydrocarbon oils in water may be gelled. For instance a solution of an active compound in oil may be emulsified into an aqueous polymerisable composition comprising the novel polymerisable derivative, and polymerisation may be initiated in the continuous phase. Active compounds are ones which have a useful effect and include herbicides, insecticides, growth promoters, biocides, pharmaceuticals, surfactants, etc. This product may be useful for providing for instance oil-soluble pheromone or weed killers in solid form. In this form, the active compounds are released over an extended period of time. This may be of use for aquatic herbicides and water-borne insecticides.

High DS polymerisable derivatives provide highly cross linked polymer, which are of particular use where a high degree of resistance to water and/or other solvents is required. As well as in chemical grouting processes, such products are useful in the production of coatings, for example protective coatings and inks. These may be cured by any conventional curing system, for instance using a photosensitive intiating system.

Copolymers with other comonomers, e.g., with acrylamide, may additionally be useful in gel filtration of biochemical compounds and in water storage applications in agriculture.

High MW low DS products may be copolymerised by reverse phase polymerisation to produce low cross-linked products. With anionic comonomers, the polymers may be useful as, for instance, flocculants for sewage. With cationic comonomers, the polymers may be useful as ply bond adhesives in, for example, paper manufacture, where they are generally found to be superior to conventional starch based pastes. With non-ionic comonomers, the polymers may be useful as non-flocculating thickeners.

In the above polymers, the polymerisable materials of the invention are generally present in an amount of from 1 to 99 mole % preferably 20 to 80 mole % and often about 50 mole %.

High DS products are useful at low levels as cross-linkers in the preparation of polymers from a wide variety of other ethylenically unsaturated water soluble monomers, for instance acrylic acid. The polymerisable products of the invention have similar cross-linking properties to methylene-bis-acrylamide, the normal cross-linking agent used but they are more water soluble.

Broadly, the products of the invention are relatively cheap, non-toxic and have a wide range of potential uses, including polymerisation uses.

The unsaturated derivatives of the invention may be reacted in processes other than polymerisation reactions. The ethylenically unsaturated bonds of the polymerisable derivatives may be reacted with suitable compounds to give ionic derivatives, for example with dimethylamine to give a tertiary amine which may be quaternised to the corresponding quaternary ammonium compound, or with dimethylsulphate. Derivatives which have an amine group in the side chain may be quaternised to give cationic groups.

Particularly preferred products are cold water soluble polysaccharides that are cationic derivatives having a degree of substitution of at least 0.1, preferably at least 0.2 and sometimes more than 0.5. Particularly preferred cationic derivatives are acid addition salts or quaternary derivatives of compounds of the formula $(HO)_mA(OCH_2NR^1COCHR^3CH_2NR^4R^5)_p$ where $A(OH)_n$ is a water-soluble carbohydrate, m is zero or, usually, a higher number, p is a number greater than zero and $m+p=n$, $R^1$ and $R^3$ are independently selected from hydrogen and lower alkyl and $R^4$ and $R^5$ are each alkyl or $R^4$ and $R^5$ together with the nitrogen atom to which they are attached form a heterocyclic ring which may contain other heteroatoms, preferably a morpholine ring, all alkyl groups generally containing 1 to 4 carbon atoms. These compounds are preferably made by direct condensation of the corresponding amino alkylamide derivative onto the substrate but may also be made by condensation of methylol acrylamide followed by addition of dialkylamino or morpholine across the ethylenically unsaturated group. Ionisation of the amino group may be by acid addition but is preferably by quaternization using, for example methyl chloride or dimethyl sulphate.

In the preferred reaction in which the derivatising reagent is a saturated compound, e.g., N-hydroxymethyl-3,3-dimethylaminopropanamide or N-hydroxymethyl-3-morpholino-propanamide, quaternisation of the tertiary amino group may be carried out after the derivatisation reaction but is preferably done before the derivatisation reaction. The substrate in these novel products is preferably dextrin, generally a white dextrin. These highly substituted cationic polysaccharides are useful as, for instance, flocculants and coagulation aids.

Another class of preferred products have at least two different substituents having different values of R. These products may be made by making a first derivative having a single type of reactive side chain and then reacting only some of the side chains to form a different group. The preferred process is to use two different derivatising reagents as the starting materials. The mixture of starting materials may be made from a single derivatising reagent which is reacted so that part only is converted to a second derivatising reagent. For example a saturated amine derivatising reagent may be partially quaternised. An unsaturated derivatising reagent may be partially reacted by addition of compounds to provide ionic groups. In the preferred process, products comprising two reactive groups are made from starting materials comprising two different derivatising reagents.

Particularly preferred products in this class have unsaturated groups and ionic groups. For example, they may comprise ethylenically unsaturated polymerisable side chains or ionic or, preferably, cationic groups. Such products are generally further reacted by polymerising, generally with other comonomers, to give ionic polymers having useful properties.

Another preferred derivative is one having quaternised and unquaternised tertiary amine groups.

A particularly preferred use of the high DS unsaturated derivative is in the production of highly water-resistant films, which may be coloured and which are generally cured by exposure to radiation, generally UV light. The composition containing the product may be used as for instance an ink.

In U.S. Pat. No. 4,079,025, there is discussed an aqueous composition comprising unsaturated starch derivatives used as a cross linker for other ethylenically unsaturated polymerisable monomers. The starch derivatives invariably require cooking to dissolve in water since they are cold-water insoluble. The method of production of the coating compositions is thus complicated. The process described in the specification is incapable of producing degrees of substitution of more than about 0.15 and we have found that the films obtained by curing such compositions did not have a satisfactory degree of water-resistance.

In GB No. 2070047, water-based inks comprise an aqueous monomer system and a water-soluble photoinitiator, generally with dye and/or pigment and other film-forming aids, optionally with other ingredients. The water soluble monomer may include acrylamide or N-methylol acrylamide. The films have only limited water-resistance and are unsatisfactory for many applications.

An aqueous composition according to the invention that can be cured by exposure to UV light comprises a water-soluble photoinitiator and a water-soluble polymerisable compound and is characterised in that the water soluble polymerisable compound has the formula $(HO)_m$—A—$(OCH_2NR^1COCR^6=CR^7R^8)_p$ in which $A(OH)_n$ is a carbohydrate as defined above, $R^1$ and $R^6$ are independently hydrogen or methyl, $R^7$ and $R^8$ are independently selected from hydrogen and lower alkyl, preferably each is hydrogen, m is zero or higher and p is a positive number and $n=m+p$.

The compositions are generally used as inks and are cured after application to a substrate by irradiation with UV light and so they are preferably coloured. Therefore the compositions generally comprise a water-soluble dye. Suitable water-soluble dyes are the reactive dyestuffs manufactured commercially for dyeing cellulosic and woollen fabrics sold under the trade-names 'Lanasol' (Ciba Geigy), 'Remazol' (Hoechst), 'Procilan' (ICI), 'Cibacron' (Ciba Geigy) and 'Drimarene' (Sandoz). Although reactive dyestuffs are to be preferred, it is possible to use other types of dye such as basic (Astazon, Bayer), direct (Chyrysophenine, L. B. Holliday & Co.) or acidic (Nylosan, Sandoz). Mixtures of dyes can be used to prepare coatings of different hues.

It is thought that the dye becomes incorporated into the polymer during curing of the compositions. Reactive groups in the dye may be ethylenically unsaturated groups, which are through to copolymerise with the polymerisable compound. The reactive group may be a triazine group which is thought to act as a chain transfer agent which terminates polymer chains and is thereby chemically bonded to the polymer. The amount of dye in the composition is preferably in the range of 0.01 to 10%, preferably 0.1 to 5% by weight of the total weight of the composition.

The polymerisable compounds should generally have a high degree of substitution, for example above 0.05, preferably above 0.1 and must preferably above 0.2 up to about 1.0. The films are water-resistant, i.e., when a drop of water is allowed to rest on the film for 1 hour, no obvious disruption or swelling of the film is observed. Also, if a portion (10 cm$^2$) of film is stirred (30 min) at room temperature, less than 10% of the colour is extracted compared with an uncured film of the same composition. Water resistance increases with increasing DS, since the polymer molecules are more high cross linked and thus less able to dissolve or swell in water.

The photoinitiator is preferably water-soluble such as

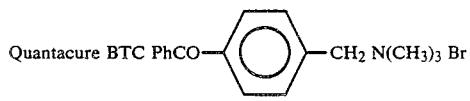

Quantacure BTC (supplied by Ward Blenkinsop Ltd.) or similar water-soluble benzophenone or benzil derivatives such as 3,3',4,4'-benxophenonetetracarboxylic dianhydride. Other suitably initiators are discussed in "Research Disclosure" February 1981, page 93. The amount may be in the range 0.01 to 10%, preferably 0.05 to 1.0% by weight based on the total weight of the composition.

The compositions may comprise water-soluble photoactivators to improve the polymerisation. Suitable activators are water-soluble amines such as triethanolamine and other water-soluble reducing agents. The composition may also comprise other components to give the desired rheology and solids content of the compositions which depend on the coating technique used for the compositions. For high colour density coatings, pigments are often included in the compositions in an amount of up to 20% or more by weight. Preferably the film forming composition is free of other curable materials, preferably free of other solvents and dispersed materials.

The following examples illustrate the invention.

EXAMPLE 1

Various solutions in water of carbohydrate and N-methylol acrylamide (NMA) are prepared by dissolution of the carbohydrate in deionised water at room temperature using mechanical stirring and then adding an acid generating catalyst. The particular carbohydrates are identified in Table 1 below. The catalyst is ammonium chloride in all instances except for Examples 1a and 1e in Table 1, when it is ammonium hydrogen phosphate. Copper nitrate is added to the aqueous phase in the amount stated in Table 1 to serve as polymerisation inhibitor and then NMA is added. The pH of the solution is approximately 4.5.

A 700 ml resin flask is equipped with a mechanical stirrer, a splash-head connected to a condenser and receiving flask, a thermometer and a dropping funnel. The flask is charged with Solvent 41 (Shell Chemical Co.) (300 g) containing stabiliser (a copolymer of stearyl methacrylate and methacrylic acid 0.2 wt % based on aqueous charge). The carbohydrate/NMA mixture (40-60 wt % in water) is drawn by partial vacuum into the solvent held at 80° C. After agitating for 5 minutes, small droplets are formed. The contents are then warmed to the desired temperature and solvent/water azeotropically distilled at this temperature by adjusting the pressure to a suitable value. Distillation is continued until no further water is collected in the distillate.

The contents of the reaction flask are cooled, the beads filtered at the pump and dried either by use of a fluid-bed drier at 50° C. or for highly substituted products, the beads are first acetone washed and dried at 30° C.

12 different acrylamido methyl derivatives were prepared by this inverse suspension method, varying only the proportion of NMA and the starting carbohydrate substrate. The amount of acid catalyst was 2.4%, the temperature of reaction was 75° C.

The carbohydrate substrates are shown in Table 1 below. Cellan is a low molecular weight water soluble product derived from cellulose by acid catalysed hydrolysis (J. Appl. Polym. Sci. Appl. Polymer Symp. 37 641–651 (1983)). Substrates A to F are Dextrins as follows:

A: low viscosity yellow dextrin
B: low viscosity white dextrin
C: medium viscosity yellow dextrin
D: medium viscosity white dextrin
E: high viscosity yellow dextrin
F: high viscosity white dextrin For low molecular weight substrates, the products were characterised by double bond titration ($Br_2$ absorption) to determine total percentage of acrylamidomethyl groups, and residual unreacted NMA by extraction with hot 80% aqueous acetone (Soxhlet) and g.l.c. From these measurements, the percentage conversion from free to bound acrylamidomethyl groups and degree of substitution (DS) of the carbohydrate substrate were calculated. In all examples cited the % bound and free NMA accounted, within experimental error, for all the NMA added to the reaction mixture the results shown in Table 1.

For high molecular weight substrates (eg F), the actual DS was calculated from the nitrogen content (Kjeldahl) of dialysed samples.

TABLE 1

| Example | Substrate | Theoretical DS | Actual DS | Cu 11 (ppm) |
|---|---|---|---|---|
| 1a | A | 0.04 | 0.01 | 5 |
| 1b | B | 0.03 | 0.01 | 5 |
| 1c | D | 0.04 | 0.01 | 5 |
| 1d | B | 0.20 | 0.06 | 5 |
| 1e | B | 0.25 | 0.09 | 5 |
| 1f | A | 0.95 | 0.22 | 250 |
| 1g | B | 1.20 | 0.26 | 250 |
| 1h | C | 1.15 | 0.25 | 500 |
| 1i | D | 0.90 | 0.22 | 500 |
| 1j | E | 1.05 | 0.24 | 500 |
| 1k | F | 1.05 | 0.24 | 500 |
| 1l | cellan | 0.22 | 0.06 | 5 |

EXAMPLE 2

The method described in Example 1 was used to prepare the acrylamidomethyl derivatives of glucose, sucrose, sorbitol and glycerol. For these substrates, higher levels of Cu(II) inhibitor were used (Table 2). Ammonium chloride was used as catalyst (2.4% on aqueous phase).

TABLE 2

| Example | Substrate | Proportion of NMA Unreacted (%) | Molar Ratio substituent/ substrate | Cu II (ppm) |
|---|---|---|---|---|
| 2a | sorbitol | 14 | 0.37 | 1000 |
| 2b | sorbitol | 15 | 1.90 | 1500 |
| 2c | D-glucose | 17 | 1.03 | 2000 |
| 2d | sucrose | 37 | 0.76 | 1500 |
| 2e | glycerol | 37 | 0.91 | 1500 |

EXAMPLE 3

The method described in Example 1, with 2000 ppm Cu II, was used to prepare the acrylamidomethyl derivative of poly(vinyl alcohol) (Gohsenol GH-17, Nippon Gohsei). Analysis showed there to be 24% of the NMA remaining unreacted and 49% of the hydroxy-groups of the polymer substituted with acrylamidomethyl groups.

Similarly, a number of monohydric, dihydric and polyhydric alcohols were converted to their acrylamidomethyl derivatives. Thus when neopentyl alcohol was used, the product was water insoluble but soluble products were obtained when using neopentyl glycol alcohol or polyethylene glycol 4000, 400 or 200.

EXAMPLE 4

The synthetic procedure described in Example 1 was used to prepare the methacrylamidomethyl derivative of dextrin B by reaction with N-methylolmethacrylamide using 1.3% $NH_4Cl$ catalyst and 100 ppm Cu II inhibitor. The product was photopolymerisable.

EXAMPLE 5

Using the process described in Example 1, beads of an aqueous phase (100 parts) containing a low viscosity yellow dextrin (33 parts), $NH_4Cl$ (1.32 parts) NMA 45% (49 parts) and methylene blue polymerisation inhibitor (0.032 part) were formed in a hydrocarbon solvent (Solvent 41, 107 parts) and dehydrated by azeotropic distillation at 85° C. The resulting beads were recovered by filtering at the pump, washing with acetone and air drying.

A 10% w/w solution (100 parts) of these beads could be polymerised by addition of aqueous ammonium persulphate (20%, 5 parts) and triethanolamine (20% 5 parts) to yield a firm gel without de-gassing. Gel times could readily be manipulated from 5–60 minutes by suitable choice of initiator and inhibitor concentrations.

When initiated in such a manner, the gel was capable of forming in the presence of solid particulate matter such as clays, sand, diatomaceous earth etc., emulsified oil droplets such as hydrocarbon oils, pinene etc. and soluble materials such as low molecular weigh poly-(sodium acrylate).

EXAMPLE 6

A 700 ml flask equipped with a stirrer, thermometer and a dropping funnel was charged with 300 g Solvent 41 and 2.9 g stabiliser (a copolymer of stearyl methacrylate and methacrylic acid; 15%) and the solution deoxygenated with $N_2$.

Acrylamidomethyl dextrin 1e (60 g) was dissolved in 51% aqueous acrylamide solution (118 g) and diluted with deionised water (22 g). After adjustment to pH 6, the aqueous monomer was dispersed into the solvent and after 5 minutes stirring small uniform beads were formed. Polymerisation was induced using redox initiator system giving a heat rise of 34° C.

The beads (average diameter approximately 0.5 mm) were dried by azeotropic distillation, recovered by filtration and dried at 80° C. in a fluid-bed drier.

After standing for 1 hour in 0.1N NaCl, the swollen beads (absorbency 4 ml/g) were packed into a 20×1 cm column and gel filtration performed using a mixture of Blue Dextran (MW several million), vitamin B12 (MW 1200) and sodium chromate as high, medium and low molecular weight markers respectively. During elution the blue, red and yellow bands could be seen to separate readily on the column showing a high resolution efficiency.

EXAMPLE 7

An aqueous phase was formulated from 88.8 g product 1c, 243.7 g deionised water, 53.3 g acrylamide and 49.5 g of 72.4% aqueous solution of dimethylaminoethyl acrylate quaternised with methyl chloride. This solution was then used as the aqueous phase in a reverse phase polymerisation process conducted in conventional manner, for instance using thermal initiator and sequestrant in the aqueous phase and using, as the oil phase, a blend of volatile and non-volatile oils such as Shell Solvent 41 and Shell Solvent Pale Oil 60 in the presence of stabiliser and emulsifier. The emulsion was formed with vigorous agitation and cooling, deoxygenated and then heated to initiate polymerisation. The product was azeotropically distilled to yield a smooth and mobile dispersion that was substantially dry and contained 50% solids. A small amount of a high HLB surfactant was added to render the dispersion more readily dispersable in water, in conventional manner.

Dispersion of this product in water produced a very low viscosity suspension of cross-linked microparticles at 1% at ambient temperatures but on warming to 45°–55° C. the mixture became very viscous. On cooling the viscosity was lost. These properties were found to be useful when the copolymer was examined as a ply-bond adhesive for laminated paper manufacture.

Another product, obtained in similar manner, was tested as a ply-bond adhesive in paper manufacture.

A product (A) similar in composition to that described above was sprayed at 2% solids in water onto the bottom sheet of a twin ply after the couch and prior to the press nip. Samples of treated paper were compared with samples made using starch slurry in the usual way.

The results (Table 3) showed that the adhesive bond was stronger than with starch even though the coat weight was 2–6 times lower (0.5 gsm vs. 1–3 gsm). However the stiffness of the test paper was much reduced, possibly as a result of poor distribution of the spray droplets.

TABLE 3

| Product | Sheet Substance (gsm) | Ply Bond (lbin$^2$) | Burst (LPa) | Stiffness (nH) |
|---|---|---|---|---|
| A | 199 | 77 | 551 | 37 |
| Starch | 194 | 66 | 581 | 117 |

EXAMPLE 8

A solution of 53 parts acrylamidomethyl dextrin 1g, 40.1 parts in water containing 4 parts Quantacure BTC, a water-soluble photo-initiator supplied by Ward Blenkinsop Ltd, 0.2 part triethanolamne and 2.7 parts water-soluble dye was coated at approximately 12 microns onto plain cardboard. Exposure to U.V. for less than 1 second caused polymerisation to occur giving a clear glossy surface coating. This film was somewhat brittle but was very water resistant.

EXAMPLE 9

A mixture was made of sub-100 micron silica (10–20 parts) and a 45% solids solution of acrylamidomethyl dextrin 1g containing 0.5% Quantacure BTC (80–90 parts) and coated at approximately 10 micron onto a sheet of Melinex S.

After exposure to U.V. light for less than 1 second, the coating had cured to a tough, strongly adhering, white-translucent film. A pencil mark was made and erased 25 times on the same spot with no obvious deterioration of the surface. This coating was impervious to water.

EXAMPLE 10

Acrylamidomethyl dextrin 1g was evaluated at low doses as a cross-linker for the preparation of poly-(sodium acrylate) water-absorbing polymers. This product was found to be superior to the lower DS derivatives and many other di- and poly-functional acrylates in producing hydrogels which have a relatively high capacity to absorb saline solutions and also it was found to be on a par with methylene-bis-(acrylamide) which sometimes causes problems during the manufacturing process because of its limited water solubility.

EXAMPLE 11

Aqueous dimethylamine (128 g, 60%) was added over a few minutes to a stirred solution of product 1k (1000 g; 28% solids) at room temperature. A temperature rise of 10° C. was observed and the pH changed from about 4 to 10.5. This reaction mixture was then drawn into a stainless steel reactor and methyl chloride gas pumped in to an overpressure of 60 p.s.i. The mixture was stirred and the temperature held below 30° C. by water cooling until no further consumption of methyl chloride occurred.

The quantity of methyl chloride taken up by the reaction mixture was measured by chloride titration against standard silver nitrate using a chloride electrode. It was found that not all the acrylamidomethyl groups had been aminated by the dimethylamine and therefore the product contained both polymerisable groups and cationic groups.

EXAMPLE 12

Morpholine (348 g) was added over a period of 5 minutes to an aqueous solution of acrylamide (54%; 522 g). External cooling was applied to maintain the temperature of the mixture below 80° C. After 2h, water (394 g) and paraformaldehyde (120 g) was added to the cooled solution. After warming to 50° C., an exothermic reaction caused the temperature to rise to 60° C. and after holding at this temperature for a further 2h, the solution of N-hydroxymethyl-morpholine propanamide thus formed was transferred to a stainless steel reaction vessel and quaternised with methyl chloride gas at 50 p.s.i. for 3h at 80° C. This product was assayed by chloride titration and found to be 55% w/w quaternised intermediate (I).

An aqueous phase consisting of high viscosity white dextrin (Perfectamyl AW 420, Tunnel AVEBE Starches Ltd.) (90 g dry basis), solution I (146 g), ammonium chloride (6 g), deionised water (150 g) and aqueous copper sulphate 1.6 ml (5% pentahydrate) was added with stirring to a solution of polymeric stabiliser (0.8 g copolymer of stearyl methacrylate/methacrylic acid 1:1 molar ratio) in a hydrocarbon solvent (500 g CAS 19/15 Shell Chemicals) to form aqueous droplets suspended in the oil phase.

On warming, the aqueous droplets formed homogeneous beads which were dehydrated by distillation under reduced pressure at 75°–80° C. until no further water was collected in the distillate. The dried beads (approximately 1 mm diameter) were filtered at the pump, washed with acetone and finally dried in a fluid bed drier at 60° C.

The product readily dissolved in cold water to give a fairly viscous 30% w/w solution. On dialysis and evaporation of this solution, a purified polymer was obtained which had 1.84%N consistent with dextrin derivatised with reagent I to a degree of substitution of 0.13.

EXAMPLE 13

In a similar procedure to that given in Example 12, acrylamide (146 g) was reacted with dimethylamine in an aqueous reaction mixture and was then reacted with formaldehyde and quaternised as before with methyl chloride to yield a 58% solution of intermediate II.

Using the same condensation process as described in Example 12, Perfectamyl AW420 (100 g dry) was reacted with 145 g of the 58% solution of intermediate II using NH$_4$Cl catalyst (6 g) in water (100 g).

The dried, beaded product was dissolved in cold water to give a moderately viscous 20% w/w solution. A sample of purified polymer was prepared by precipitation with methanol (1 volume). On dissolution in water and titration with standard silver nitrate solution, the purified polymer was found to contain 2.4% Cl, consistent with derivatisation with reagent II to a degree of substitution of 0.12.

We claim:

1. A process for forming an ether between a water soluble N-methylol amide and a water soluble polyol that has the formula A(OH)n where n is a positive number of at least 3 and that is selected from sugar alcohols, carbohydrates and synthetic hydroxy substituted polymers, the process comprising forming a dispersion in a water immiscible liquid of 25 to 75%, by volume of the dispersion, of an aqueous solution of the N-methylol amide, a catalytic amount of an acid condensation catalyst and the polyol in an amount of 10 to 80% by weight of the aqueous solution, maintaining the temperature at at least 60° C. to cause condensation between the methylol groups of the said N-methylol amide with the polyol and the formation of the said ether with the elimination of water, and azeotroping the dispersion while at the said temperature to remove eliminated water and to drive the condensation reaction towards completion.

2. A process according to claim 1 wherein the N-methylol amide has the formula HOCH$_2$NR$^1$COR$^2$ wherein R$^1$ is hydrogen or C$_{1-4}$ alkyl and R$^2$ is an alkenyl or alkyl group.

3. A process according to claim 1 in which the polyol is selected from polyvinyl alcohol, polyethylene glycol, sugar alcohol and polysaccharide having molecular weight above 1,000.

4. A process according to claim 1 in which the polyol is a water soluble polysaccharide having molecular weight above 10,000.

5. A process according to claim 1 in which the polyol is a water soluble dextrin.

6. A process according to claim 1 in which the N-methylol amide is selected from N-methylol acrylamide and methylol methacrylamide.

7. A process according to claim 1 in which the methylol amide includes an ethylenically unsaturated group and the aqueous solution includes a polymerization inhibitor.

8. A process according to claim 7 in which the polymerization inhibitor comprises Cu (II) ion.

9. A process according to claim 1 in which the polyol is a polysaccharide and the resulting ether has a degree of substitution of at least 0.1.

10. A process according to claim 1 in which the polyol is a polysaccharide and the resulting ether has a degree of substitution of at least 0.2.

11. A process according to claim 1 in which the resulting ether will form a true solution or a stable colloidal solution with no solid residue when dissolved in water at a concentration of 20% and a temperature of 20° C.

12. A process according to claim 1 in which the the methylol amide is formed in situ in the aqueous phase of the reaction mixture by reaction of formaldehyde with the corresponding amide.

* * * * *